(12) United States Patent
Yang et al.

(10) Patent No.: US 10,472,490 B2
(45) Date of Patent: *Nov. 12, 2019

(54) THERMOPLASTIC RESIN COMPOSITION AND ARTICLE PRODUCED THEREFORM

(71) Applicant: Lotte Advanced Materials Co., Ltd., Yeosu-si (KR)

(72) Inventors: Cheon Seok Yang, Uiwang-si (KR); Yoen Kyoung Kim, Uiwang-si (KR); Seung Yong Bae, Uiwang-si (KR); Ju Sung Kim, Uiwang-si (KR)

(73) Assignee: Lotte Advanced Materials Co., Ltd., Yeosu-si (KR)

( * ) Notice: Subject to any disclaimer, the term of this patent is extended or adjusted under 35 U.S.C. 154(b) by 81 days.

This patent is subject to a terminal disclaimer.

(21) Appl. No.: 15/790,334

(22) Filed: Oct. 23, 2017

(65) Prior Publication Data

US 2018/0112056 A1  Apr. 26, 2018

(30) Foreign Application Priority Data

Oct. 25, 2016  (KR) .................. 10-2016-0138997
Jun. 15, 2017  (KR) .................. 10-2017-0075940

(51) Int. Cl.

| | | |
|---|---|---|
| *C08K 3/22* | (2006.01) | |
| *C08K 5/00* | (2006.01) | |
| *C08L 67/00* | (2006.01) | |
| *C08L 77/00* | (2006.01) | |
| *C08F 8/42* | (2006.01) | |
| *C08F 12/02* | (2006.01) | |
| *C08F 20/18* | (2006.01) | |
| *B29C 45/00* | (2006.01) | |
| *G01N 23/20* | (2018.01) | |

(52) U.S. Cl.
CPC .............. *C08K 3/22* (2013.01); *C08F 8/42* (2013.01); *C08F 12/02* (2013.01); *C08F 20/18* (2013.01); *C08K 5/0016* (2013.01); *C08L 67/00* (2013.01); *C08L 77/00* (2013.01); *B29C 45/0001* (2013.01); *C08K 2003/2296* (2013.01); *C08K 2201/003* (2013.01); *C08K 2201/006* (2013.01); *C08L 2205/24* (2013.01); *G01N 23/20* (2013.01)

(58) Field of Classification Search
CPC .... C01G 9/03; C08K 3/22; C08K 2003/2296; C08L 55/02; C08L 25/12
See application file for complete search history.

(56) References Cited

U.S. PATENT DOCUMENTS

| | | |
|---|---|---|
| 3,041,303 A | 6/1962 | Nelson |
| 3,354,108 A | 11/1967 | Paradis et al. |
| 4,331,786 A | 5/1982 | Foy et al. |
| 4,356,300 A | 10/1982 | Isler et al. |
| 4,612,340 A | 9/1986 | Ohachi |
| 5,714,534 A | 2/1998 | Kojima et al. |
| 5,714,545 A | 2/1998 | Lee et al. |
| 5,906,679 A | 5/1999 | Watanabe et al. |
| 6,166,116 A | 12/2000 | Sleeckx |
| 6,297,307 B1 | 10/2001 | Eichenauer et al. |
| 6,663,877 B1 | 12/2003 | Appleton et al. |
| 8,128,998 B2 | 3/2012 | Li et al. |
| 2002/0106413 A1 | 8/2002 | Herbst et al. |
| 2002/0109805 A1 | 8/2002 | Baba |
| 2003/0125413 A1 | 7/2003 | Herbst et al. |
| 2005/0043485 A1 | 2/2005 | Lee et al. |
| 2005/0131100 A1 | 6/2005 | Herbst et al. |
| 2007/0009691 A1 | 1/2007 | Barre et al. |
| 2007/0049678 A1 | 3/2007 | Kim et al. |
| 2010/0264383 A1 | 10/2010 | Tooley et al. |
| 2014/0017335 A1 | 1/2014 | Dimov et al. |
| 2016/0326670 A1 | 11/2016 | Kang et al. |
| 2017/0198132 A1 | 7/2017 | Choi et al. |
| 2018/0112056 A1 | 4/2018 | Yang et al. |
| 2018/0118914 A1* | 5/2018 | Bae .................... C08K 3/22 |
| 2018/0179314 A1* | 6/2018 | Kim .................... C08L 33/12 |

(Continued)

FOREIGN PATENT DOCUMENTS

| | | |
|---|---|---|
| CN | 1710153 A | 12/2005 |
| CN | 1919542 A | 2/2007 |
| CN | 101001805 A | 7/2007 |

(Continued)

OTHER PUBLICATIONS

Tsai (The Influence on Intensity Ratio of Peak Emission between Recombination of Free-Excitons and Deep-Defect for ZnO Nanostructure Evolution from Nanorods to Nanotubes. Proceedings of the 16th International Conference on Nanotechnology, Sendai, Japan. Aug. 22-25, 2016, pp. 387-389).*
Machine translated English language equivalent of CN 101880426 (2010, 5 pages).*
Machine translated English language equivalent of JP 2014221708 (2014, 9 pages).*
Extended Search Report in counterpart European Application No. 17198304.2 dated Mar. 12, 2018, pp. 1-5.
Database WPI, Week 201654, Thomson Scientific, London, GB, Abstract of Korean Publication No. 2016-0083527 (Kolon Plastics Inc.) Jul. 12, 2016, pp. 1-2.
Office Action in counterpart Taiwanese Application No. 106136641 dated Aug. 17, 2018, pp. 1-6.

(Continued)

*Primary Examiner* — Brieann R Johnston
(74) *Attorney, Agent, or Firm* — Additon, Higgins & Pendleton, P.A.

(57) ABSTRACT

A thermoplastic resin composition and a molded article produced therefrom. The thermoplastic resin composition includes about 100 parts by weight of a thermoplastic resin and about 0.5 to about 30 parts by weight of zinc oxide. The zinc oxide has a peak intensity ratio (B/A) of about 0.1 to about 1.0, wherein A indicates a peak in the wavelength range of 370 nm to 390 nm and B indicates a peak in the wavelength range of 450 nm to 600 nm in photoluminescence measurement. The thermoplastic resin composition can exhibit good properties in terms of weather resistance, antibacterial properties, and the like.

19 Claims, No Drawings

(56) References Cited

U.S. PATENT DOCUMENTS

2018/0179373 A1* 6/2018 Kim .................. C08L 25/12
2018/0186989 A1 7/2018 Lee et al.

FOREIGN PATENT DOCUMENTS

| | | | |
|---|---|---|---|
| CN | 101880426 A | * | 11/2010 |
| CN | 107974030 A | | 5/2018 |
| EP | 1190622 A1 | | 3/2002 |
| EP | 1510549 A1 | | 3/2005 |
| EP | 3026082 A1 | | 6/2016 |
| EP | 3326975 A1 | | 5/2018 |
| EP | 3339367 A1 | | 6/2018 |
| EP | 3339370 A1 | | 6/2018 |
| FR | 1439417 A | | 5/1966 |
| GB | 1040287 A | | 8/1966 |
| JP | 55-133424 A | | 10/1980 |
| JP | 56-045419 A | | 4/1981 |
| JP | 08-253640 A | | 10/1996 |
| JP | 10-182927 | | 7/1998 |
| JP | H10195309 A | | 7/1998 |
| JP | 10-251444 A | | 9/1998 |
| JP | 11-035787 A | | 2/1999 |
| JP | 2001-220486 A | | 8/2001 |
| JP | 2006-182841 A | | 7/2006 |
| JP | 2014-172783 | | 9/2014 |
| JP | 2014221708 A | * | 11/2014 |
| JP | 2016-121273 A | | 7/2016 |
| KR | 10-2002-0008203 A | | 1/2002 |
| KR | 10-0696385 B1 | | 3/2007 |
| KR | 10-2007-0047073 A | | 5/2007 |
| KR | 10-2010-0087603 A | | 8/2010 |
| KR | 10-1334283 B1 | | 11/2013 |
| KR | 10-1452020 B1 | | 10/2014 |
| KR | 2016-0083527 | | 7/2016 |

OTHER PUBLICATIONS

Office Action in counterpart Korean Application No. 10-2017-0075940 dated Aug. 21, 2017, pp. 1-8.
Prasanna et al., "Insight into the Mechanism of Antibacterial Activity of ZnO: Surface Defects Mediated Reactive Oxygen Species Even in the Dark", ACS Publications, Langmuir 2015, 31, pp. 9155-9162.
Search Report in commonly owned European Application No. 17210669.2 dated Apr. 20, 2018, pp. 1-5.
Office Action in commonly owned Korean Application No. 10-2016-0184170 dated Sep. 6, 2018, pp. 1-6.
Extended Search Report in commonly owned European Application No. 17209267.8 dated Mar. 26, 2018, pp. 1-7.
Office Action in commonly owned Korean Application No. 10-2016-0176575 dated Nov. 1, 2018, pp. 1-7.
Office Action in commonly owned Korean Application No. 10-2017-0111807 dated Nov. 27, 2018, pp. 1-9.
Chandrakanth et al., "Synthesis and characterization of ZnO nanorods with a narrow size distribution", Royal Society of Chemistry, 2015, vol. 5, pp. 49861-49870 (17 pages).
Extended Search Report in commonly owned European Application No. 17199720.8 dated Mar. 7, 2018, pp. 1-7.
Database WPI, Week 201463, Thomson Scientific, London, GB, Abstract of JP 2014-172783 (UBE Kagaku Kogyo KK), pp. 1-2.
Office Action in commonly owned Korean Application No. 10-2016-0177857 dated Nov. 20, 2018, pp. 1-8.
Extended Search Report in commonly owned European Application No. 17210117.2, dated Apr. 30, 2018, pp. 1-5.
Office Action in commonly owned U.S. Appl. No. 15/798,819 dated May 13, 2019, pp. 1-20.
Office Action in commonly owned U.S. Appl. No. 15/845,020 dated Aug. 8, 2019, pp. 1-13.
Machine translated English language equivalent of JP Application No. H09-212736, which is the same as publication JP 11-035787 (1999, 10 pages).
Machine translated English language equivalent of CN 191542 (2007, 5 pages).
Office Action in counterpart Chinese Application No. 201711007395.8 dated Jul. 31, 2019, pp. 1-6.
Office Action in commonly owned Chinese Application No. 201711062077.1 dated Jul. 12, 2019, pp. 1-7.
Office Action in commonly owned U.S. Appl. No. 15/844,980 dated Sep. 11, 2019, pp.1-5.
Machine translated English language equivalent of H09-061580, which is the same as JP Publication JP 10-251444 (1998, 14 pages).

* cited by examiner

THERMOPLASTIC RESIN COMPOSITION AND ARTICLE PRODUCED THEREFROM

CROSS-REFERENCE TO RELATED APPLICATION

This application claims priority under 35 USC Section 119 to and the benefit of Korean Patent Application 10-2016-0138997, filed Oct. 25, 2016, and Korean Patent Application 10-2017-0075940, filed Jun. 15, 2017, the entire disclosure of each of which is incorporated herein by reference.

FIELD

The present invention relates to a thermoplastic resin composition and a molded article produced therefrom.

BACKGROUND

Recently, demand for thermoplastic resin products having an antibacterial function has increased corresponding to increasing income levels and attention to personal health and hygiene. Hence, thermoplastic resin products subjected to antibacterial treatment so as to suppress or remove bacteria from surfaces of daily supplies and electronic products have increased in number, and it is a very important issue to develop an antibacterial material (antibacterial thermoplastic resin composition) having stability and reliability.

Antibacterial agents can be added to a thermoplastic resin composition to impart antibacterial properties thereto. Antibacterial agents can be classified as organic antibacterial agents and inorganic antibacterial agents.

Although organic antibacterial agents can be relatively inexpensive and can provide good antibacterial effects even with a small amount, organic antibacterial agents can often exhibit toxicity to the human body, provide inherent antibacterial effects against specific bacteria, and decompose and lose inherent antibacterial effects upon processing at high temperature. Moreover, organic antibacterial agents can cause discoloration after processing and can provide short antibacterial durability due to a problem of elution. Thus, organic antibacterial agents can be very restrictively applied to antibacterial thermoplastic resin compositions.

Inorganic antibacterial agents include an antibacterial agent containing a metallic component, such as silver (Ag) or copper (Cu). Although inorganic antibacterial agents are broadly used in the preparation of antibacterial thermoplastic resin compositions (antibacterial resins) due to good thermal stability thereof, inorganic antibacterial agents are generally required to be added in large amounts due to lower antibacterial effects than organic antibacterial agents. Moreover, inorganic antibacterial agents can have many problems, such as relatively high price, difficulty in uniform dispersion during processing, and discoloration due to the metallic component, and can have many limitations in use.

Therefore, there is a need for a thermoplastic resin composition which can secure good properties in terms of weather resistance (discoloration resistance), antibacterial properties (bacteria resistance) and antibacterial durability and can realize antifungal properties.

SUMMARY OF THE INVENTION

Exemplary embodiments provide a thermoplastic resin composition that can exhibit good properties in terms of weather resistance, antibacterial properties (bacteria resistance), and/or mechanical properties, and a molded article produced therefrom.

The thermoplastic resin composition includes: about 100 parts by weight of a thermoplastic resin; and about 0.5 to about 30 parts by weight of zinc oxide, the zinc oxide having a peak intensity ratio (B/A) of about 0.1 to about 1.0, wherein A indicates a peak in the wavelength range of 370 nm to 390 nm and B indicates a peak in the wavelength range of 450 nm to 600 nm in photoluminescence measurement.

In exemplary embodiments, the zinc oxide may have a peak position degree (2θ) in the range of 35° to 37° and a crystallite size of about 1,000 Å to about 2,000 Å in analysis of X-ray diffraction (XRD), as calculated by Equation 1:

$$\text{Crystallite size}(D) = \frac{K\lambda}{\beta\cos\theta} \quad \text{[Equation 1]}$$

wherein, K is a shape factor, λ is an X-ray wavelength, β is an FWHM value (degree) of an X-ray diffraction peak, and θ is a peak position degree.

In exemplary embodiments, the zinc oxide may be prepared by melting zinc particles in a reactor, heating the molten zinc to about 850° C. to about 1,000° C. to vaporize the molten zinc, injecting oxygen gas into the reactor, cooling the reactor to about 20° C. to about 30° C., and heating the reactor to about 400° C. to about 900° C. for about 30 minutes to about 150 minutes.

In exemplary embodiments, the thermoplastic resin may include at least one of a rubber-modified vinyl-based copolymer resin, a polyolefin resin, an aromatic vinyl resin, a polycarbonate resin, a poly(alkyl (meth)acrylate) resin, a polyester resin, and a polyamide resin.

In exemplary embodiments, the rubber-modified vinyl-based copolymer resin may include a rubber-modified vinyl graft copolymer and an aromatic vinyl copolymer resin.

In exemplary embodiments, the rubber-modified vinyl graft copolymer may be prepared by graft polymerization of an aromatic vinyl monomer and a monomer copolymerizable with the aromatic vinyl monomer to a rubber polymer.

In exemplary embodiments, the aromatic vinyl copolymer resin may be a copolymer of an aromatic vinyl monomer and a monomer copolymerizable with the aromatic vinyl monomer.

In exemplary embodiments, the zinc oxide may have a peak intensity ratio (B/A) of about 0.2 to about 1.0 in photoluminescence measurement.

In exemplary embodiments, the zinc oxide may have a peak intensity ratio (B/A) of about 0.2 to about 0.7 in photoluminescence measurement.

In exemplary embodiments, the zinc oxide may have an average particle diameter (D50) of about 0.5 μm to about 3 μm, as measured by a particle analyzer.

In exemplary embodiments, the zinc oxide may have an average particle diameter (D50) of about 1 μm to about 3 μm, as measured by a particle analyzer.

In exemplary embodiments, the zinc oxide may have a BET specific surface area of about 10 m²/g or less, as measured by a nitrogen gas adsorption method using a BET analyzer.

In exemplary embodiments, the zinc oxide may have a BET specific surface area of about 1 m²/g to about 7 m²/g, as measured by a nitrogen gas adsorption method using a BET analyzer.

In exemplary embodiments, the thermoplastic resin composition may have a color variation (ΔE) of about 2 to about 12, as calculated according to Equation 2:

$$\text{Color variation } (\Delta E) = \sqrt{(\Delta L^*)^2 + (\Delta a^*)^2 + (\Delta b^*)^2} \quad \text{[Equation 2]}$$

wherein, ΔL* is a difference (L1*-L0*) between L* values before/after temperature/humidity testing; Δa* is a difference (a1*-a0*) between a* values before/after temperature/humidity testing; and Δb* is a difference (b1*-b0*) between b* values before/after temperature/humidity testing, in which L0*, a0* and b0* are initial color values, as measured on an injection molded specimen having a size of 50 mm×90 mm×3 mm in accordance with ASTM D4459, and L1*, a1* and b1* are color values, as measured on the specimen in accordance with ASTM D4459 after exposure under conditions of 85° C. and 85% relative humidity (RH) for 200 hours.

In exemplary embodiments, the thermoplastic resin composition may include a rubber-modified vinyl-based copolymer resin as the thermoplastic resin and have a color variation (ΔE) of about 7 to about 10.

In exemplary embodiments, the thermoplastic resin composition may include a polyolefin resin as the thermoplastic resin and have a color variation (ΔE) of about 2 to about 3.3.

In exemplary embodiments, the thermoplastic resin composition may include an aromatic vinyl resin as the thermoplastic resin and have a color variation (ΔE) of about 10 to about 12.

In exemplary embodiments, the thermoplastic resin composition may have an antibacterial activity of about 2 to about 7, as measured by an antibacterial evaluation method in accordance with JIS Z 2801 and calculated by Equation 3:

$$\text{Antibacterial activity} = \log(M1/M2) \quad \text{[Equation 3]}$$

wherein, M1 is the number of bacteria measured on a blank specimen after culturing for 24 hours and M2 is the number of bacteria measured on a specimen of the thermoplastic resin composition after culturing for 24 hours, in which each specimen has a size of 5 cm×5 cm and is prepared by inoculation with each of *Staphylococcus aureus* and *Escherichia coli*, followed by culturing under conditions of 35° C. and 90% RH for 24 hours.

Other embodiments relate to a molded article. The molded article is formed of the thermoplastic resin composition.

DETAILED DESCRIPTION

The above and other aspects, features, and advantages of the present invention will become apparent from the detailed description of the following embodiments. It should be understood that the present invention is not limited to the following embodiments and may be embodied in different ways, and that the embodiments are provided for complete disclosure and thorough understanding of the present invention by those skilled in the art. The scope of the present invention should be defined only by the appended claims.

Hereinafter, embodiments of the present invention will be described in detail.

A thermoplastic resin composition according to the present invention includes: (A) a thermoplastic resin; and (B) zinc oxide.

(A) Thermoplastic Resin

According to exemplary embodiments, the thermoplastic resin may be a thermoplastic resin used for a typical thermoplastic resin composition. Examples of the thermoplastic resin may include without limitation a rubber-modified vinyl-based copolymer resin, a polyolefin resin, an aromatic vinyl resin, a polycarbonate resin, a poly(alkyl (meth)acrylate) resin, a polyester resin, a polyamide resin, and the like, and combinations and/or mixtures thereof. For example, the thermoplastic resin may include (A1) a rubber-modified vinyl-based copolymer resin, (A2) a polyolefin resin, (A3) an aromatic vinyl resin, and/or a combination and/or mixture thereof.

(A1) Rubber-Modified Vinyl-Based Copolymer Resin

According to exemplary embodiments, the rubber-modified vinyl-based copolymer resin may include (A1-1) a rubber-modified vinyl graft copolymer and (A1-2) an aromatic vinyl copolymer resin.

(A1-1) Rubber-Modified Vinyl Graft Copolymer

According to exemplary embodiments, the rubber-modified vinyl graft copolymer may be prepared by graft polymerization of an aromatic vinyl monomer and a monomer copolymerizable with the aromatic vinyl monomer to a rubber polymer.

In this embodiment, the rubber-modified vinyl graft copolymer may be prepared by adding the aromatic vinyl monomer and the monomer copolymerizable with the aromatic vinyl monomer to the rubber polymer, followed by polymerization. Here, the polymerization may be performed by any typical polymerization method known in the art, such as emulsion polymerization, suspension polymerization, and mass polymerization.

Examples of the rubber polymer may include diene rubbers such as polybutadiene, poly(styrene-butadiene), and/or poly(acrylonitrile-butadiene); saturated rubbers obtained by adding hydrogen to the diene rubbers; isoprene rubbers; acrylic rubbers such as poly(butyl acrylate); ethylene-propylene-diene monomer terpolymer (EPDM), and the like, without being limited thereto. These may be used alone or as a mixture thereof. For example, the rubber polymer may be a diene rubber, for example a butadiene rubber.

The rubber-modified vinyl graft copolymer can include rubber polymer in an amount of about 5% by weight (wt %) to about 65 wt %, for example, about 10 wt % to about 60 wt %, and as another example about 20 wt % to about 50 wt %, based on the total weight (100 wt %) of the rubber-modified vinyl graft copolymer. In some embodiments, the rubber-modified vinyl graft copolymer can include the rubber polymer in an amount of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 wt %. Further, according to some embodiments, the amount of the rubber polymer can be in a range from about any of the foregoing amounts to about any other of the foregoing amounts.

Within this range, the thermoplastic resin composition can exhibit good properties in terms of impact resistance, mechanical properties, and the like.

The rubber polymer (rubber particles) may have an average (z-average) particle diameter of about 0.05 μm to about 6 μm, for example, about 0.15 μm to about 4 μm, and as another example about 0.25 μm to about 3.5 μm. Within this range, the thermoplastic resin composition can exhibit good properties in terms of impact resistance, appearance, flame retardancy, and the like. As used herein, the average (z-average) particle size was measured by a dry method known in the art using a Mastersizer 2000E series tester (Malvern).

The aromatic vinyl monomer is graft-copolymerizable with the rubber polymer and may include, for example, styrene, α-methylstyrene, β-methylstyrene, p-methylstyrene, p-t-butylstyrene, ethylstyrene, vinylxylene, monochlorostyrene, dichlorostyrene, dibromostyrene, vinyl naphthalene, and the like, without being limited thereto. These may be used alone or as a mixture thereof.

The rubber-modified vinyl graft copolymer can include the aromatic vinyl monomer in an amount of about 15 wt % to about 94 wt %, for example, about 20 wt % to about 80 wt %, and as another example about 30 wt % to about 60 wt %, based on the total weight (100 wt %) of the rubber-modified vinyl graft copolymer. In some embodiments, the rubber-modified vinyl graft copolymer can include the aromatic vinyl monomer in an amount of about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, or 94 wt %. Further, according to some embodiments, the amount of the aromatic vinyl monomer can be in a range from about any of the foregoing amounts to about any other of the foregoing amounts.

Within this range, the thermoplastic resin composition can exhibit good properties in terms of fatigue resistance, impact resistance, mechanical properties, and the like.

Examples of the monomer copolymerizable with the aromatic vinyl monomer may include vinyl cyanide compounds, such as acrylonitrile, methacrylonitrile, ethacrylonitrile, phenylacrylonitrile, α-chloroacrylonitrile, and/or fumaronitrile, (meth)acrylic acid and/or alkyl esters thereof, maleic anhydride, N-substituted maleimide, and the like, without being limited thereto. As used herein, the term "alkyl" refers to C1-C10 alkyl. These may be used alone or as a mixture thereof. In exemplary embodiments, the monomer copolymerizable with the aromatic vinyl monomer may be acrylonitrile, methyl (meth)acrylate, or a combination thereof.

The rubber-modified vinyl graft copolymer can include the monomer copolymerizable with the aromatic vinyl monomer in an amount of about 1 wt % to about 50 wt %, for example, about 5 wt % to about 45 wt %, and as another example about 10 wt % to about 30 wt %, based on the total weight (100 wt %) of the rubber-modified vinyl graft copolymer. In some embodiments, the rubber-modified vinyl graft copolymer can include the monomer copolymerizable with the aromatic vinyl monomer in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt %. Further, according to some embodiments, the amount of the monomer copolymerizable with the aromatic vinyl monomer can be in a range from about any of the foregoing amounts to about any other of the foregoing amounts.

Within this range, the thermoplastic resin composition can exhibit good properties in terms of impact resistance, flowability, appearance, and the like.

Examples of the rubber-modified vinyl graft copolymer may include acrylonitrile-butadiene-styrene graft copolymer (g-ABS) in which a styrene monomer as the aromatic vinyl compound and an acrylonitrile monomer as the vinyl cyanide compound are grafted to a butadiene rubber polymer, and/or methyl methacrylate-butadiene-styrene graft copolymer (g-MBS) in which a styrene monomer as the aromatic vinyl compound and methyl methacrylate as the monomer copolymerizable with the aromatic vinyl compound are grafted to a butadiene rubber polymer, without being limited thereto.

In exemplary embodiments, the rubber-modified vinyl-based copolymer resin (A1) can include the rubber-modified vinyl graft copolymer (A1-1) in an amount of about 10 wt % to about 40 wt %, for example, about 15 wt % to about 30 wt %, based on the total weight (100 wt %) of the rubber-modified vinyl-based copolymer resin (A1). In some embodiments, the rubber-modified vinyl-based copolymer resin (A1) can include the rubber-modified vinyl graft copolymer (A1-1) in an amount of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 wt %. Further, according to some embodiments, the amount of the rubber-modified vinyl graft copolymer can be in a range from about any of the foregoing amounts to about any other of the foregoing amounts.

Within this range, the thermoplastic resin composition can exhibit good properties in terms of impact resistance, flowability (moldability), and the like.

(A1-2) Aromatic Vinyl Copolymer Resin

According to exemplary embodiments, the aromatic vinyl copolymer resin may be an aromatic vinyl copolymer resin used in a typical rubber-modified vinyl-based copolymer resin. For example, the aromatic vinyl copolymer resin may be a polymer of a monomer mixture including an aromatic vinyl monomer and a monomer copolymerizable with the aromatic vinyl monomer, such as a vinyl cyanide monomer.

In exemplary embodiments, the aromatic vinyl copolymer resin may be prepared by mixing the aromatic vinyl monomer and the monomer copolymerizable with the aromatic vinyl monomer, followed by polymerization of the mixture. Here, the polymerization may be performed by any typical polymerization method known in the art, such as emulsion polymerization, suspension polymerization, and mass polymerization.

In exemplary embodiments, the aromatic vinyl monomer may include styrene, α-methylstyrene, β-methylstyrene, p-methylstyrene, p-t-butylstyrene, ethylstyrene, vinylxylene, monochlorostyrene, dichlorostyrene, dibromostyrene, vinyl naphthalene, and the like, without being limited thereto. These may be used alone or as a mixture thereof.

The aromatic vinyl copolymer resin can include aromatic vinyl monomer in an amount of about 20 wt % to about 90 wt %, for example, about 30 wt % to about 80 wt %, based on the total weight (100 wt %) of the aromatic vinyl copolymer resin. In some embodiments, the aromatic vinyl copolymer resin can include aromatic vinyl monomer in an amount of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 wt %. Further, according to some embodiments, the amount of the aromatic vinyl monomer can be in a range from about any of the foregoing amounts to about any other of the foregoing amounts.

Within this range, the thermoplastic resin composition can exhibit good properties in terms of impact resistance, flowability, and the like.

Examples of the monomer copolymerizable with the aromatic vinyl monomer may include vinyl cyanide compounds, such as acrylonitrile, methacrylonitrile, ethacrylonitrile, phenylacrylonitrile, α-chloroacrylonitrile, and/or fumaronitrile, (meth)acrylic acid and/or alkyl esters thereof, maleic anhydride, N-substituted maleimide, and the like, without being limited thereto. As used herein, the term "alkyl" refers to C1-C10 alkyl. These may be used alone or as a mixture thereof.

The aromatic vinyl copolymer resin can include the monomer copolymerizable with the aromatic vinyl monomer in an amount of about 10 wt % to about 80 wt %, for example, about 20 wt % to about 70 wt %, based on the total weight (100 wt %) of the aromatic vinyl copolymer resin. In some embodiments, the aromatic vinyl copolymer resin can include the monomer copolymerizable with the aromatic vinyl monomer in an amount of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 wt %. Further, according to some embodiments, the amount of the monomer copolymerizable with the aromatic vinyl monomer can be in a range from about any of the foregoing amounts to about any other of the foregoing amounts.

Within this range, the thermoplastic resin composition can exhibit good properties in terms of impact resistance, flowability, and the like.

In exemplary embodiments, the aromatic vinyl copolymer resin may have a weight average molecular weight (Mw) of about 10,000 g/mol to about 300,000 g/mol, for example, about 15,000 g/mol to about 15,000 g/mol, as measured by gel permeation chromatography (GPC). Within this range, the thermoplastic resin composition can exhibit good properties in terms of mechanical properties, moldability, and the like.

In exemplary embodiments, the rubber-modified vinyl-based copolymer resin (A1) can include the aromatic vinyl copolymer resin (A1-2) in an amount of about 60 wt % to about 90 wt %, for example, about 70 wt % to about 85 wt %, based on the total weight (100 wt %) of the rubber-modified vinyl-based copolymer resin (A1). In some embodiments, the rubber-modified vinyl-based copolymer resin (A1) can include the aromatic vinyl copolymer resin (A1-2) in an amount of 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 wt %. Further, according to some embodiments, the amount of the aromatic vinyl copolymer resin can be in a range from about any of the foregoing amounts to about any other of the foregoing amounts.

Within this range, the thermoplastic resin composition can exhibit good properties in terms of impact resistance, flowability (moldability), and the like.

(A2) Polyolefin Resin

According to exemplary embodiments, the polyolefin resin may be a typical polyolefin resin. Examples of the polyolefin may include without limitation: polyethylene-based resins such as low density polyethylene (LDPE), middle density polyethylene (MDPE), high density polyethylene (HDPE), linear low density polyethylene (LLDPE), ethylene-vinyl acetate (EVA) copolymer, ethylene-acrylate copolymer, and the like, and mixtures thereof; polypropylene resins such as polypropylene, propylene-ethylene copolymer, propylene-1-butane copolymer, and the like, and mixtures thereof; polymers obtained by crosslinking the same; a blend containing polyisobutane; and the like, and mixtures thereof. For example, a polypropylene resin may be used as the polyolefin resin.

In exemplary embodiments, the polyolefin resin may have a weight average molecular weight (Mw) of about 10,000 to about 400,000 g/mol, for example, about 15,000 to about 350,000 g/mol, as measured by gel permeation chromatography (GPC). Within this range, the thermoplastic resin composition can exhibit good properties in terms of mechanical properties, moldability, and the like.

(A3) Aromatic Vinyl Resin

According to exemplary embodiments, the aromatic vinyl resin may be a typical aromatic vinyl resin. For example, the aromatic vinyl resin may include polystyrene (PS), high impact polystyrene (HIPS), styrene-acrylonitrile copolymer resin (SAN), and the like. These may be used alone or as a mixture thereof. The aromatic vinyl resin may be prepared by a typical method known to those skilled in the art or may be obtained from commercially available products.

In exemplary embodiments, the aromatic vinyl resin may have a weight average molecular weight (Mw) of about 10,000 to about 300,000 g/mol, for example, about 15,000 to about 250,000 g/mol, as measured by gel permeation chromatography (GPC). Within this range, the thermoplastic resin composition can exhibit good properties in terms of mechanical properties, moldability, and the like.

(B) Zinc Oxide

According to the present invention, zinc oxide serves to improve weather resistance and antibacterial properties (bacterial resistance) of the thermoplastic resin composition, and may have a peak intensity ratio (B/A) of about 0.1 to about 1.0, for example, about 0.2 to about 1.0, and as another example about 0.2 to about 0.7, wherein A indicates a peak in the wavelength range of 370 nm to 390 nm and B indicates a peak in the wavelength range of 450 nm to 600 nm in photoluminescence measurement. If the intensity ratio (B/A) of the zinc oxide is less than about 0.1, the thermoplastic resin composition can suffer from deterioration in antibacterial properties, and if the intensity ratio (B/A) of the zinc oxide exceeds about 1.0, the thermoplastic resin composition can suffer from initial discoloration of the thermoplastic resin and deterioration in weather resistance.

In exemplary embodiments, the zinc oxide may have a peak position degree (2θ) in the range of 35° to 37° and a crystallite size of about 1,000 Å to about 2,000 Å, for example, about 1,200 Å to about 1,800 Å in analysis of X-ray diffraction (XRD), as calculated by Scherrer's Equation (Equation 1) with reference to a measured FWHM value (full width at half maximum of a diffraction peak). Within this range, the thermoplastic resin composition can exhibit good properties in terms of initial color, weather resistance (discoloration resistance), antibacterial properties, and balance of mechanical properties.

$$\text{Crystallite size}(D) = \frac{K\lambda}{\beta\cos\theta} \qquad \text{[Equation 1]}$$

wherein, K is a shape factor, λ is an X-ray wavelength, β is an FWHM value (degree) of an X-ray diffraction peak, and θ is a peak position degree.

In exemplary embodiments, the zinc oxide may have various shapes, for example, a spherical shape, a plate shape, a rod shape, and the like, and combinations thereof. Further, the zinc oxide may have an average particle diameter (D50) of about 0.5 μm to about 3 μm, for example, about 1 μm to about 3 μm, as measured in a single particle state (not forming a secondary particle through agglomeration of particles) using a particle analyzer (Laser Diffraction Particle Size Analyzer LS I3 320, Beckman Coulter Co., Ltd.). In some embodiments, the zinc oxide may have an average particle diameter (D50) of about 0.5, 0.6, 0.7, 0.8, 0.9, 1, 2, or 3 μm. Within this range of particle size, the thermoplastic resin composition can exhibit good properties in terms of discoloration resistance, weather resistance, and the like.

In exemplary embodiments, the zinc oxide may have a BET specific surface area of about 10 m$^2$/g or less, for example, about 1 m²/g to about 7 m²/g, as measured by a nitrogen gas adsorption method using a BET analyzer (Surface Area and Porosity Analyzer ASAP 2020, Micromeritics Co., Ltd.), and a purity of about 99% or more. Within this range, the thermoplastic resin composition can exhibit good properties in terms of mechanical properties, discoloration resistance, and the like.

In exemplary embodiments, the zinc oxide may be prepared by melting zinc particles in a reactor, heating the molten zinc to about 850° C. to about 1,000° C., for example, about 900° C. to about 950° C., to vaporize the molten zinc, injecting oxygen gas into the reactor, cooling the reactor to about 20° C. to about 30° C., and heating the reactor to about 400° C. to about 900° C., for example, about 500° C. to about 800° C., for about 30 minutes to about 150 minutes, for example, about 60 minutes to about 120 minutes.

In exemplary embodiments, the thermoplastic resin composition may include the zinc oxide in an amount of about 0.5 to about 30 parts by weight, for example, about 0.5 to about 20 parts by weight, and as another example about 1 to about 10 parts by weight, relative to about 100 parts by weight of the thermoplastic resin. In some embodiments, the thermoplastic resin composition can include the zinc oxide in an amount of about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 parts by weight. Further, according to some embodiments, the amount of the zinc oxide can be in a range from about any of the foregoing amounts to about any other of the foregoing amounts.

If the zinc oxide is present in an amount of less than about 0.5 parts by weight relative to about 100 parts by weight of the thermoplastic resin, the thermoplastic resin composition can suffer from deterioration in weather resistance, antibacterial properties (bacteria resistance), and the like, and if the zinc oxide is present in an amount of larger than about 30 parts by weight, the thermoplastic resin composition can suffer from deterioration in mechanical properties and the like.

The thermoplastic resin composition according to one embodiment may further include one or more optional additives, which are included in a typical thermoplastic resin composition. Examples of the additives may include flame retardants, fillers, antioxidants, anti-dripping agents, lubricants, release agents, nucleating agents, antistatic agents, stabilizers, pigments, dyes, and the like, and mixtures and/or combinations thereof, without being limited thereto. The additives may be present in an amount of about 0.001 to about 40 parts by weight, for example, about 0.1 to about 10 parts by weight, relative to about 100 parts by weight of the thermoplastic resin.

The thermoplastic resin composition may be prepared in pellet form by mixing the aforementioned components, followed by melt extrusion using a typical twin-screw extruder at about 200° C. to about 280° C., for example, about 220° C. to about 250° C.

In exemplary embodiments, the thermoplastic resin composition may have a color variation (ΔE) of about 2 to about 12, as calculated according to Equation 2.

$$\text{Color variation }(\Delta E)=\sqrt{(\Delta L^*)^2+(\Delta a^*)^2+(\Delta b^*)^2} \quad \text{[Equation 2]}$$

wherein, ΔL* is a difference (L1*−L0*) between L* values before/after temperature/humidity testing; Δa* is a difference (a1*−a0*) between a* values before/after temperature/humidity testing; and Δb* is a difference (b1*−b0*) between b* values before/after temperature/humidity testing, in which L0*, a0* and b0* are initial color values, as measured on an injection molded specimen having a size of 50 mm×90 mm×3 mm in accordance with ASTM D4459, and L1*, a1* and b1* are color values, as measured on the specimen in accordance with ASTM D4459 after exposure under conditions of 85° C. and 85% RH for 200 hours.

Δa* may range from about 1.0 to about 1.5. If Δa* is not within this range, weather resistance (discoloration resistance) of the thermoplastic resin composition can be significantly deteriorated to allow color variation to be observed with the naked eye.

In exemplary embodiments, the thermoplastic resin composition may include a rubber-modified vinyl-based copolymer resin as the thermoplastic resin and have a color variation (ΔE) of about 7 to about 10, for example, about 7.5 to about 9.

In exemplary embodiments, the thermoplastic resin composition may include a polyolefin resin as the thermoplastic resin and have a color variation (ΔE) of about 2 to about 3.3, for example, about 2.1 to about 3.

In exemplary embodiments, the thermoplastic resin composition may include an aromatic vinyl resin as the thermoplastic resin and have a color variation (ΔE) of about 10 to about 12, for example, about 10.5 to about 11.5.

In exemplary embodiments, the thermoplastic resin composition has antibacterial effects against various bacteria, such as *Staphylococcus aureus, Escherichia coli, Bacillus subtilis, Pseudomonas aeruginosa, salmonella, pneumococcus*, MRSA (methicillin-resistant *Staphylococcus aureus*), and the like, and may independently have an antibacterial activity of about 2 to about 7, for example, about 2 to about 6.5, and as another example about 4 to about 6.5, as measured by an antibacterial evaluation method in accordance with JIS Z 2801 and calculated by Equation 3.

$$\text{Antibacterial activity}=\log(M1/M2) \quad \text{[Equation 3]}$$

wherein, M1 is the number of bacteria measured on a blank specimen after culturing for 24 hours and M2 is the number of bacteria measured on a specimen of the thermoplastic resin composition after culturing for 24 hours, in which each specimen has a size of 5 cm×5 cm and is prepared by inoculation with each of *Staphylococcus aureus* and *Escherichia coli*, followed by culturing under conditions of 35° C. and 90% RH for 24 hours.

The term "blank specimen" refers to a control specimen with respect to a test specimen (specimen of the thermoplastic resin composition). Specifically, in order to confirm normal growth of inoculated bacteria, the blank specimen can be prepared by inoculating a petri dish with bacteria, followed by culturing for 24 hours in the same way as in the preparation of the test specimen. The antibacterial effect of the test specimen is determined by comparing the number of bacteria cultured thereon. Further, the number of bacteria can be counted after a process of culturing the inoculated bacteria on each specimen for 24 hours and diluting the cultured bacteria liquid, followed by growing into colonies on the petri dish. When it is difficult to count the number of bacteria due to an excessive number of colonies, the number of bacteria can be counted and converted into an actual number of bacteria after division into several regions.

In exemplary embodiments, the thermoplastic resin composition may include a rubber-modified vinyl-based copolymer resin as the thermoplastic resin and may have an Izod impact strength of about 14 kgf·cm/cm to about 30 kgf·cm/cm, as measured on an injection-molded ⅛" thick specimen in accordance with ASTM D256.

In exemplary embodiments, the thermoplastic resin composition may include a polyolefin resin the thermoplastic resin and may have an Izod impact strength of about 4 kgf·cm/cm to about 15 kgf·cm/cm, as measured on an injection-molded 1/8" thick specimen in accordance with ASTM D256.

In exemplary embodiments, the thermoplastic resin composition may include an aromatic vinyl resin as the thermoplastic resin and may have an Izod impact strength of about 7 kgf·cm/cm to about 20 kgf·cm/cm, as measured on an injection-molded 1/8" thick specimen in accordance with ASTM D256.

Exemplary embodiments also relate to a molded article formed of the thermoplastic resin composition as set forth above. The antibacterial thermoplastic resin composition may be prepared in pellet form. The prepared pellets may be formed into a molded article (product) by various molding methods such as injection molding, extrusion, vacuum molding, and/or casting. Such molding methods are well known to those skilled in the art. The molded article can exhibit good properties in terms of weather resistance, antibacterial properties (bacteria resistance), impact resistance, flowability (moldability), and balance therebetween, and thus may be applied to antibacterial products, exterior materials, and the like, which are frequently brought into contact with the human body.

Next, the present invention will be described in more detail with reference to the following examples. It should be understood that these examples are provided for illustration only and are not to be construed in any way as limiting the present invention.

EXAMPLE

Details of components used in the Examples and Comparative Examples are as follows.

(A) Thermoplastic resin (A1) Rubber-modified vinyl-based copolymer resin

A rubber-modified vinyl-based copolymer resin comprising 27 wt % of a rubber-modified vinyl graft copolymer (A1-1) and 73 wt % of an aromatic vinyl copolymer resin (A1-2) is used.

(A1-1) Rubber-modified vinyl graft copolymer

A g-ABS resin prepared by grafting 55 wt % of styrene and acrylonitrile (weight ratio: 75/25) to 45 wt % of polybutadiene rubber (PBR) particles having a Z-average particle diameter of 310 nm is used.

(A1-2) Aromatic vinyl copolymer resin

A styrene-acrylonitrile (SAN) resin (weight average molecular weight: 130,000 g/mol) prepared by polymerization of 68 wt % styrene and 32 wt % acrylonitrile is used.

(A2) Polyolefin resin

A polypropylene resin having a weight average molecular weight of 248,600 g/mol (Manufacturer: Lotte Chemical Co., Ltd.) is used.

(A3) Aromatic vinyl resin

A high flowability HIPS having a weight average molecular weight of 160,000 g/mol (H-834, Dongbu Chemical Co., Ltd.) is used.

(B) Zinc oxide (B1) Zinc oxide prepared by melting zinc particles in a reactor, heating the molten zinc to 900° C. to vaporize the molten zinc, injecting oxygen gas into the reactor, and cooling the reactor to room temperature (25° C.) to form an intermediate material, followed by heat treatment of the intermediate material at 700° C. for 90 minutes and cooling the heat-treated material to room temperature (25° C.) is used.

(B2) Zinc oxide (KS-1, PJ ChemTek Co., Ltd.) is used.

(B3) Zinc oxide (RZ-950, Ristecbiz Co., Ltd.) is used.

For each of the zinc oxides B1, B2 and B3, an average particle diameter, BET surface area, purity, a peak intensity ratio (B/A) of peak A in the wavelength range of 370 nm to 390 nm to peak B in the wavelength range of 450 nm to 600 nm in photoluminescence measurement, and crystallite size are measured, and measurement results are shown in Table 1.

(B4) Zinc oxide prepared by melting zinc particles in a reactor, heating the molten zinc to 900° C. to vaporize the molten zinc, injecting oxygen gas into the reactor, and cooling the reactor to room temperature (25° C.) to form an intermediate material, followed by heat treatment of the intermediate material at 800° C. for 90 minutes and cooling the heat-treated material to room temperature (25° C.) is used.

(B5) Zinc oxide prepared by melting zinc particles in a reactor, heating the molten zinc to 900° C. to vaporize the molten zinc, injecting oxygen gas into the reactor, and cooling the reactor to room temperature (25° C.) to form an intermediate material, followed by heat treatment of the intermediate material at 500° C. for 90 minutes and cooling the heat-treated material to room temperature (25° C.) is used.

(B6) Zinc oxide prepared by heat treatment of zinc oxide (RZ-950, Ristecbiz Co., Ltd.) at 700° C. for 90 minutes and cooling the heat-treated zinc oxide to room temperature (25° C.) is used.

For each of the zinc oxides B1, B2, B3, B4, B5 and B6, an average particle diameter, BET surface area, purity, a peak intensity ratio (B/A) of peak A in the wavelength range of 370 nm to 390 nm to peak B in the wavelength range of 450 nm to 600 nm in photoluminescence (PL) measurement, and crystallite size are measured, and measurement results are shown in Table 1.

TABLE 1

| | (B1) | (B2) | (B3) | (B4) | (B5) | (B6) |
|---|---|---|---|---|---|---|
| Average particle diameter (μm) | 1.2 | 1.0 | 1.1 | 1.2 | 1.2 | 1.2 |
| BET surface area (m²/g) | 4 | 6 | 15 | 4.2 | 4.1 | 14.9 |
| Purity (%) | 99 | 99 | 97 | 99 | 99 | 99 |
| PL peak intensity ratio (B/A) | 0.28 | 0.05 | 9.8 | 0.11 | 0.98 | 1.61 |
| Crystallite size (Å) | 1417 | 1229 | 503 | 1420 | 1451 | 519 |

Property Evaluation (1) Average particle diameter (unit: μm): Average particle diameter (volume average) is measured using a particle analyzer (Laser Diffraction Particle Size Analyzer LS 13 320, Beckman Coulter Co., Ltd.).

(2) BET surface area (unit: m²/g): BET surface area is measured by a nitrogen gas adsorption method using a BET analyzer (Surface Area and Porosity Analyzer ASAP 2020, Micromeritics Co., Ltd.).

(3) Purity (unit: %): Purity is measured by thermogravimetric analysis (TGA) based on the weight of remaining material at 800° C.

(4) PL peak intensity ratio (B/A): Spectrum emitted upon irradiation of a specimen using a He—Cd laser (KIMMON, 30 mW) at a wavelength of 325 nm is detected by a CCD detector in a photoluminescence measurement method, in which the CCD detector is maintained at −70° C. A peak intensity ratio (B/A) of peak A in the wavelength range of 370 nm to 390 nm to peak B in the wavelength range of 450 nm to 600 nm is measured. Here, an injection molded specimen is irradiated with laser beams without separate treatment upon PL analysis, and zinc oxide powder is compressed in a pelletizer having a diameter of 6 mm to prepare a flat specimen.

(5) Crystallite size (unit: Å): Crystallite size is measured using a high-resolution X-ray diffractometer (PRO-MRD, X'pert Inc.) at a peak position degree (2θ) in the range of 35° to 37° and calculated by Scherrer's Equation (Equation 1) with reference to a measured FWHM value (full width at half maximum of a diffraction peak). Here, both a powder form and an injection molded specimen could be measured. For more accurate analysis, the injection molded specimen is subjected to heat treatment at 600° C. in air for 2 hours to remove a polymer resin therefrom before XRD analysis.

$$\text{Crystallite size}(D) = \frac{K\lambda}{\beta\cos\theta} \quad \text{[Equation 1]}$$

wherein, K is a shape factor, λ is an X-ray wavelength, β is an FWHM value (degree) of an X-ray diffraction peak, and θ is a peak position degree.

Examples 1 to 12 and Comparative Examples 1 to 24

The above components are mixed in amounts as listed in Tables 2 to 6, followed by melt extrusion at 230° C., thereby preparing a thermoplastic resin composition in pellet form. Extrusion is performed using a twin-screw extruder (L/D=36, φ=45 mm). The prepared pellets are dried at 80° C. for 4 hours or more, followed by injection molding using a 6 oz. injection molding machine at a molding temperature of 230° C. and a mold temperature of 60° C., thereby preparing a specimen. The prepared specimen is evaluated as to the following properties and results are shown in Tables 2 to 6.

Evaluation Method (1) Weather resistance (color variation (ΔE)): For calculation of color difference, initial color values L0*, a0* and b0* are measured on an injection molded specimen having a size of 50 mm×90 mm×3 mm in accordance with ASTM D4459, and color values L1*, a1* and b1* are measured on the specimen in accordance with ASTM D4459 after exposure under conditions of 85° C. and 85% RH for 200 hours. Color variation (ΔE) is calculated by Equation 2.

$$\text{Color variation }(\Delta E) = \sqrt{(\Delta L^*)^2 + (\Delta a^*)^2 + (\Delta b^*)^2} \quad \text{[Equation 2]}$$

wherein, ΔL* is a difference (L1*−L0*) between L* values before/after temperature/humidity testing; Δa* is a difference (a1*−a0*) between a* values before/after temperature/humidity testing; and Δb* is a difference (b1*−b0*) between b* values before/after temperature/humidity testing.

(2) Antibacterial activity: Antibacterial activity is measured by an antibacterial evaluation method in accordance with JIS Z 2801 and calculated by Equation 3. Each specimen having a size of 5 cm×5 cm is prepared by inoculation with each of *Staphylococcus aureus* and *Escherichia coli*, followed by culturing under conditions of 35° C. and 90% RH for 24 hours.

$$\text{Antibacterial activity} = \log(M1/M2) \quad \text{[Equation 3]}$$

wherein, M1 is the number of bacteria measured on a blank specimen after culturing for 24 hours and M2 is the number of bacteria measured on a specimen of the thermoplastic resin composition after culturing for 24 hours.

(3) Impact resistance (notched Izod impact strength (unit: kgf·cm/cm)): Notched Izod impact strength is measured on a ⅛" thick specimen in accordance with ASTM D256.

TABLE 2

| | Example | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| (A1) (parts by weight) | 100 | 100 | — | — | — | — | 100 | 100 | — | — | — | — |
| (A2) (parts by weight) | — | — | 100 | 100 | — | — | — | — | 100 | 100 | — | — |
| (A3) (parts by weight) | — | — | — | — | 100 | 100 | — | — | — | — | 100 | 100 |
| (B1) (parts by weight) | 2 | 25 | 2 | 25 | 2 | 25 | — | — | — | — | — | — |
| (B4) (parts by weight) | — | — | — | — | — | — | 10 | — | 10 | — | 10 | — |
| (B5) (parts by weight) | — | — | — | — | — | — | — | 10 | — | 10 | — | 10 |
| Δa* | 1.16 | 1.40 | 0.12 | 0.07 | 2.41 | 2.21 | 1.21 | 1.22 | 0.14 | 0.18 | 1.31 | 1.48 |
| Color variation (ΔE) | 8.03 | 8.41 | 2.41 | 2.29 | 10.98 | 10.76 | 8.11 | 8.12 | 2.51 | 2.93 | 11.10 | 11.31 |
| Antibacterial activity (*Escherichia coli*) | 4.6 | 4.6 | 4.6 | 4.6 | 4.6 | 4.6 | 4.6 | 4.6 | 4.6 | 4.6 | 4.6 | 4.6 |
| Antibacterial activity (*Staphylococcus aureus*) | 6.4 | 6.4 | 6.4 | 6.4 | 6.4 | 6.4 | 6.4 | 6.4 | 6.4 | 6.4 | 6.4 | 6.4 |

TABLE 3

| | Comparative Example | | | | | | | |
|---|---|---|---|---|---|---|---|---|
| | 1 | 2 | 3 | 4 | 5 | 6 | 7 | 8 |
| (A1) (parts by weight) | 100 | 100 | 100 | 100 | 100 | 100 | 100 | 100 |
| (B1) (parts by weight) | — | — | — | — | — | — | 0.1 | 31 |
| (B2) (parts by weight) | 2 | 25 | — | — | — | — | — | — |
| (B3) (parts by weight) | — | — | 2 | 25 | — | — | — | — |
| (B6) (parts by weight) | — | — | — | — | 2 | 25 | — | — |
| Δa* | 1.30 | 1.23 | 4.60 | 4.55 | 4.53 | 4.61 | 1.53 | 1.98 |
| Color variation (ΔE) | 11.18 | 11.01 | 11.91 | 11.78 | 12.10 | 11.98 | 12.78 | 10.81 |
| Antibacterial activity (*Escherichia coil*) | 3.6 | 4.6 | 3.0 | 4.5 | 3.3 | 4.6 | 0.8 | 4.6 |
| Antibacterial activity (*Staphylococcus aureus*) | 3.1 | 4.1 | 3.8 | 4.0 | 3.3 | 3.8 | 0.6 | 6.3 |

TABLE 4

| | Comparative Example | | | | | | | |
|---|---|---|---|---|---|---|---|---|
| | 9 | 10 | 11 | 12 | 13 | 14 | 15 | 16 |
| (A2) (parts by weight) | 100 | 100 | 100 | 100 | 100 | 100 | 100 | 100 |
| (B1) (parts by weight) | — | — | — | — | — | — | 0.1 | 31 |
| (B2) (parts by weight) | 2 | 25 | — | — | — | — | — | — |
| (B3) (parts by weight) | — | — | 2 | 25 | — | — | — | — |
| (B6) (parts by weight) | — | — | — | — | 2 | 25 | — | — |
| Δa* | 0.21 | 0.17 | 2.84 | 2.14 | 2.71 | 2.22 | 0.27 | 0.41 |
| Color variation (ΔE) | 4.52 | 4.30 | 6.78 | 6.07 | 6.54 | 6.19 | 10.11 | 3.41 |
| Antibacterial activity (*Escherichia coil*) | 3.4 | 4.6 | 2.8 | 4.6 | 2.4 | 4.4 | 0.2 | 4.6 |
| Antibacterial activity (*Staphylococcu saureus*) | 3.1 | 4.0 | 3.0 | 3.9 | 2.8 | 4.0 | 0.5 | 6.4 |

TABLE 5

| | Comparative Example | | | | | | | |
|---|---|---|---|---|---|---|---|---|
| | 17 | 18 | 19 | 20 | 21 | 22 | 23 | 24 |
| (A3) (parts by weight) | 100 | 100 | 100 | 100 | 100 | 100 | 100 | 100 |
| (B1) (parts by weight) | — | — | — | — | — | — | 0.1 | 31 |
| (B2) (parts by weight) | 2 | 25 | — | — | — | — | — | — |
| (B3) (parts by weight) | — | — | 2 | 25 | — | — | — | — |
| (B6) (parts by weight) | — | — | — | — | 2 | 25 | — | — |
| Δa* | 2.71 | 2.33 | 5.61 | 4.88 | 5.81 | 4.77 | 1.51 | 2.01 |
| Color variation (ΔE) | 13.11 | 13.41 | 18.69 | 17.11 | 19.01 | 16.95 | 7.88 | 10.80 |
| Antibacterial activity (*Escherichia coil*) | 3.4 | 4.6 | 3.0 | 4.6 | 2.4 | 4.4 | 0.3 | 4.6 |
| Antibacterial activity (*Staphylococcus aureus*) | 2.8 | 4.1 | 3.3 | 3.6 | 2.6 | 3.9 | 0.7 | 6.4 |

TABLE 6

| | Example | | | | | | Comparative Example | | |
|---|---|---|---|---|---|---|---|---|---|
| | 1 | 2 | 3 | 4 | 5 | 6 | 8 | 16 | 24 |
| (A1) (parts by weight) | 100 | 100 | — | — | — | — | 100 | — | — |
| (A2) (parts by weight) | — | — | 100 | 100 | — | — | — | 100 | — |
| (A3) (parts by weight) | — | — | — | — | 100 | 100 | — | — | 100 |
| (B1) (parts by weight) | 2 | 25 | 2 | 25 | 2 | 25 | 31 | 31 | 31 |
| Notched Izod impact strength | 24.2 | 15.8 | 6.7 | 4.4 | 12.1 | 7.9 | 13.2 | 3.6 | 6.4 |

From Tables 2 to 6, it can be seen that the thermoplastic resin compositions of Examples exhibit good properties in terms of weather resistance (color variation (ΔE)), antibacterial properties (antibacterial activity), mechanical properties (impact resistance), and the like.

Conversely, it can be seen that the thermoplastic resin compositions of Comparative Examples 1 and 2 prepared using a rubber-modified vinyl-based copolymer resin as the thermoplastic resin and the zinc oxide B2 having a PL peak intensity ratio (B/A) of less than 0.1 (0.05) have low weather resistance and an antibacterial activity (*Staphylococcus aureus*) of 3.1 or 4.1, which is lower than the antibacterial activity of the thermoplastic resin compositions of Examples 1 and 2. The thermoplastic resin compositions of Comparative Examples 3 and 4 prepared using the zinc oxide B3 having a BET surface area of larger than 10 m²/g (15 m²/g), a PL peak intensity ratio (B/A) of greater than 1 (9.83) and a small crystallite size (503 Å) have lower antibacterial properties (antibacterial activity) than the thermoplastic resin compositions of Examples 1 and 2, and suffer from deterioration in weather resistance and severe discoloration, as observed with the naked eye. The thermoplastic resin compositions of Comparative Examples 5 and 6 prepared using the zinc oxide B6 having a BET surface area of larger than 10 m²/g (14.9 m²/g), a PL peak intensity ratio (B/A) of greater than 1 (1.61) and a small crystallite size (519 Å) have lower antibacterial properties (antibacterial activity) than the thermoplastic resin compositions of Examples 1 and 2, and suffer from deterioration in weather resistance and severe discoloration, as observed with the naked eye. The thermoplastic resin composition of Comparative Example 7 prepared using a small amount of the zinc oxide B1 suffers from deterioration in weather resistance and severe deterioration in antibacterial properties, and the thermoplastic resin composition of Comparative Example 8 prepared using an excess of the zinc oxide B1 has lower weather resistance and mechanical properties (Table 6) than the thermoplastic resin compositions of Examples 1 and 2.

In addition, the thermoplastic resin compositions of Comparative Examples 9 and 10 prepared using a polyolefin resin as the thermoplastic resin and the zinc oxide B2 have lower weather resistance and antibacterial activity (*Staphylococcus aureus*) than the thermoplastic resin compositions of Examples 3 and 4. The thermoplastic resin compositions of Comparative Examples 11 and 12 prepared using the zinc oxide B3 suffer from deterioration in antibacterial properties (antibacterial activity) and have lower weather resistance than the thermoplastic resin compositions of Examples 3 and 4. The thermoplastic resin compositions of Comparative Examples 13 and 14 prepared using the zinc oxide B6 have lower antibacterial properties (antibacterial activity) and weather resistance than the thermoplastic resin compositions of Examples 3 and 4. Further, the thermoplastic resin composition of Comparative Example 15 prepared using a small amount of the zinc oxide B1 suffers from deterioration in weather resistance (color variation) and severe deterioration in antibacterial properties, and the thermoplastic resin composition of Comparative Example 16 prepared using an excess of the zinc oxide B1 has lower weather resistance and mechanical properties (Table 6) than the thermoplastic resin compositions of Examples 3 and 4.

Further, the thermoplastic resin compositions of Comparative Examples 17 and 18 prepared using an aromatic vinyl resin as the thermoplastic resin and the zinc oxide B2 suffer from severe deterioration in weather resistance and have lower antibacterial activity (*Staphylococcus aureus*) than the thermoplastic resin compositions of Examples 5 and 6. The thermoplastic resin compositions of Comparative Examples 19 and 20 prepared using the zinc oxide B3 have lower antibacterial properties (antibacterial activity) than the thermoplastic resin compositions of Examples 5 and 6 and suffer from severe deterioration in weather resistance. The thermoplastic resin compositions of Comparative Examples 21 and 22 prepared using the zinc oxide B6 have lower antibacterial properties (antibacterial activity) than the thermoplastic resin compositions of Examples 5 and 6 and suffer from severe deterioration in weather resistance. Further, the thermoplastic resin composition of Comparative Example 23 prepared using a small amount of the zinc oxide B1 suffers from severe deterioration in antibacterial properties, and the thermoplastic resin composition of Comparative Example 24 prepared using an excess of the zinc oxide B1 has lower mechanical properties (Table 6) than the thermoplastic resin compositions of Examples 5 and 6.

Exemplary embodiments have been disclosed herein, and although specific terms are employed, they are to be interpreted in a generic and descriptive sense only and not for purpose of limitation. Also although some embodiments have been described above, it should be understood that these embodiments are provided for illustration only and are not to be construed in any way as limiting the present invention, and that various modifications, changes, alterations, and equivalent embodiments can be made by those skilled in the art without departing from the spirit and scope of the invention. The scope of the present invention should be defined by the appended claims and equivalents thereof.

What is claimed is:

1. A thermoplastic resin composition comprising:
   about 100 parts by weight of a thermoplastic resin; and
   about 0.5 to about 30 parts by weight of zinc oxide, the zinc oxide having a peak intensity ratio (B/A) of about 0.1 to about 1.0,
   wherein A indicates intensity of the peak in the wavelength range of 370 nm to 390 nm and B indicates intensity of the peak in the wavelength range of 450 nm to 600 nm in photoluminescence measurement.

2. The thermoplastic resin composition according to claim 1, wherein the zinc oxide has a peak position degree (2θ) in the range of 35° to 37° and a crystallite size of about 1,000 Å to about 2,000 Å in analysis of X-ray diffraction (XRD), as calculated by Equation 1:

$$\text{Crystallite size } (D) = \frac{K\lambda}{\beta \cos\theta}, \quad \text{[Equation 1]}$$

wherein, K is a shape factor, λ is an X-ray wavelength, β is an FWHM value (degree) of an X-ray diffraction peak, and θ is a peak position degree.

3. The thermoplastic resin composition according to claim 1, wherein the zinc oxide is prepared by melting zinc particles in a reactor, heating the molten zinc to about 850° C. to about 1,000° C. to vaporize the molten zinc, injecting oxygen gas into the reactor, cooling the reactor to about 20° C. to about 30° C., and heating the reactor to about 400° C. to about 900° C. for about 30 minutes to about 150 minutes.

4. The thermoplastic resin composition according to claim 1, wherein the thermoplastic resin comprises at least one of a rubber-modified vinyl-based copolymer resin, an aromatic vinyl resin, a polyolefin resin, a polycarbonate resin, a poly(alkyl (meth)acrylate) resin, a polyester resin, and a polyamide resin.

5. The thermoplastic resin composition according to claim 4, wherein the rubber-modified vinyl-based copolymer resin comprises a rubber-modified vinyl graft copolymer and an aromatic vinyl copolymer resin.

6. The thermoplastic resin composition according to claim 5, wherein the rubber-modified vinyl graft copolymer is prepared by graft polymerization of an aromatic vinyl monomer and a monomer copolymerizable with the aromatic vinyl monomer to a rubber polymer.

7. The thermoplastic resin composition according to claim 5, wherein the aromatic vinyl copolymer resin is a polymer of an aromatic vinyl monomer and a monomer copolymerizable with the aromatic vinyl monomer.

8. The thermoplastic resin composition according to claim 1, wherein the zinc oxide has a peak intensity ratio (B/A) of about 0.2 to about 1.0 in photoluminescence measurement.

9. The thermoplastic resin composition according to claim 1, wherein the zinc oxide has a peak intensity ratio (B/A) of about 0.2 to about 0.7 in photoluminescence measurement.

10. The thermoplastic resin composition according to claim 1, wherein the zinc oxide has an average particle diameter (D50) of about 0.5 μm to about 3 μm, as measured by a particle analyzer.

11. The thermoplastic resin composition according to claim 1, wherein the zinc oxide has an average particle diameter (D50) of about 1 μm to about 3 μm, as measured by a particle analyzer.

12. The thermoplastic resin composition according to claim 1, wherein the zinc oxide has a BET specific surface area of about 10 m²/g or less, as measured by a nitrogen gas adsorption method using a BET analyzer.

13. The thermoplastic resin composition according to claim 1, wherein the zinc oxide has a BET specific surface area of about 1 m²/g to about 7 m²/g, as measured by a nitrogen gas adsorption method using a BET analyzer.

14. The thermoplastic resin composition according to claim 1, wherein the thermoplastic resin composition has a color variation (ΔE) of about 2 to about 12, as calculated according to Equation 2:

$$\text{Color variation } (\Delta E) = \sqrt{(\Delta L^*)^2 + (\Delta a^*)^2 + (\Delta b^*)^2}, \quad [\text{Equation 2}]$$

wherein, ΔL* is a difference (L1*−L0*) between L* values before/after temperature/humidity testing; Δa* is a difference (a1*−a0*) between a* values before/after temperature/humidity testing; and Δb* is a difference (b1*−b0*) between b* values before/after temperature/humidity testing, in which L0*, a0* and b0* are initial color values, as measured on an injection molded specimen having a size of 50 mm×90 mm×3 mm in accordance with ASTM D4459, and L1*, a1* and b1* are color values, as measured on the specimen in accordance with ASTM D4459 after exposure under conditions of 85° C. and 85% RH for 200 hours.

15. The thermoplastic resin composition according to claim 14, wherein the thermoplastic resin composition comprises a rubber-modified vinyl-based copolymer resin as the thermoplastic resin and has a color variation (ΔE) of about 7 to about 10.

16. The thermoplastic resin composition according to claim 14, wherein the thermoplastic resin composition comprises a polyolefin resin as the thermoplastic resin and has a color variation (ΔE) of about 2 to about 3.3.

17. The thermoplastic resin composition according to claim 14, wherein the thermoplastic resin composition comprises an aromatic vinyl resin as the thermoplastic resin and has a color variation (ΔE) of about 10 to about 12.

18. The thermoplastic resin composition according to claim 1, wherein the thermoplastic resin composition has an antibacterial activity of about 2 to about 7, as measured by an antibacterial evaluation method in accordance with JIS Z 2801 and calculated by Equation 3:

$$\text{Antibacterial activity} = \log(M1/M2), \quad [\text{Equation 3}]$$

wherein, M1 is the number of bacteria measured on a blank specimen after culturing for 24 hours and M2 is the number of bacteria measured on a specimen of the thermoplastic resin composition after culturing for 24 hours, in which each specimen has a size of 5 cm×5 cm and is prepared by inoculation with each of *Staphylococcus aureus* and *Escherichia coli*, followed by culturing under conditions of 35° C. and 90% RH for 24 hours.

19. A molded article formed of the thermoplastic resin composition according to claim 1.

\* \* \* \* \*